(12) United States Patent
Martin et al.

(10) Patent No.: US 9,476,818 B1
(45) Date of Patent: Oct. 25, 2016

(54) METHOD AND APPARATUS FOR HIGH SENSITIVITY PARTICULATE DETECTION IN INFRARED DETECTOR ASSEMBLIES

(71) Applicant: Raytheon Company, Waltham, MA (US)

(72) Inventors: Chadwick B. Martin, Tucson, AZ (US); Rex M. Kremer, Tucson, AZ (US); Jesse C. Temkin, Tucson, AZ (US)

(73) Assignee: Raytheon Company, Waltham, MA (US)

( * ) Notice: Subject to any disclaimer, the term of this patent is extended or adjusted under 35 U.S.C. 154(b) by 0 days.

(21) Appl. No.: 14/863,016

(22) Filed: Sep. 23, 2015

(51) Int. Cl.
*G01N 15/14* (2006.01)

(52) U.S. Cl.
CPC ................. *G01N 15/1434* (2013.01)

(58) Field of Classification Search
CPC ................................ G01N 15/1434
See application file for complete search history.

(56) References Cited

U.S. PATENT DOCUMENTS

| | | | | |
|---|---|---|---|---|
| 4,885,463 A | * | 12/1989 | Wellman | G01J 5/522 250/252.1 |
| 5,175,432 A | * | 12/1992 | Reitman | G01M 11/00 250/252.1 |
| 5,471,055 A | * | 11/1995 | Costanzo | G01J 5/522 250/252.1 |
| 8,378,290 B1 | * | 2/2013 | Speake | H04N 5/33 250/252.1 |
| 8,427,642 B2 | | 4/2013 | Mitchell et al. | |
| 8,634,054 B2 | | 1/2014 | Vladimirsky et al. | |

* cited by examiner

*Primary Examiner* — Christine Sung (57) ABSTRACT

A detector assembly includes a dewar chamber having an aperture and an infrared radiation detector. The detector assembly also includes a mirror disposed adjacent the aperture of the dewar chamber, where the mirror has a reflective surface and an emitting region facing the aperture. The infrared radiation detector is configured to detect first radiation and second radiation from the mirror. The first radiation originates from at least one relatively cold surface in the dewar chamber and reflects off the reflective surface of the mirror. The second warm radiation originates from at least one relatively warm surface at or behind the emitting region. The infrared radiation detector is also configured to detect an artifact caused by a particle in the dewar chamber that blocks a portion of the first or second radiation.

20 Claims, 6 Drawing Sheets

METHOD AND APPARATUS FOR HIGH SENSITIVITY PARTICULATE DETECTION IN INFRARED DETECTOR ASSEMBLIES

GOVERNMENT RIGHTS

This invention was made with U.S. Government support under contract number N00024-07-C-6119 awarded by the U.S. Navy. The U.S. Government may have certain rights in this invention.

TECHNICAL FIELD

This disclosure is directed in general to particulate detection. More specifically, this disclosure relates to a method and apparatus for high sensitivity particulate detection in infrared detector assemblies.

BACKGROUND

Infrared (IR) focal plane array (FPA) technology is improving rapidly and significantly. Systems utilizing IR FPA technology are becoming more sensitive to incident IR radiation and are therefore also becoming more sensitive to particulate contamination within a detector assembly. For example, individual particles on the order of only a few microns in size could produce video artifacts that affect a system's ability to acquire or track a target of interest. Current particle screen tests at the detector assembly level have poor sensitivity compared to sensor level tests and therefore often miss the presence of harmful particles, which can necessitate expensive and risky rework of detector assemblies.

SUMMARY

This disclosure provides a method and apparatus for high sensitivity particulate detection in infrared detector assemblies.

In a first embodiment, a detector assembly includes a dewar chamber having an aperture and an infrared radiation detector. The detector assembly also includes a mirror disposed adjacent the aperture of the dewar chamber, where the mirror has a reflective surface and an emitting region facing the aperture. The infrared radiation detector is configured to detect first radiation and second radiation from the mirror. The first radiation originates from at least one relatively cold surface in the dewar chamber and reflects off the reflective surface of the mirror. The second warm radiation originates from at least one relatively warm surface at or behind the emitting region. The infrared radiation detector is also configured to detect an artifact caused by a particle in the dewar chamber that blocks a portion of the first or second radiation.

In a second embodiment, a method includes detecting, at an infrared radiation detector, first radiation originating from at least one relatively cold surface in a dewar chamber and reflecting off a reflective surface of a mirror. The method also includes detecting, at the infrared radiation detector, second radiation originating from at least one relatively warm surface at or behind an emitting region of the mirror. The method also includes detecting, at the infrared radiation detector, an artifact caused by a particle in the dewar chamber that blocks a portion of the first or second radiation. The infrared radiation detector is disposed in the dewar chamber, and the dewar chamber includes an aperture. The mirror is disposed adjacent the aperture of the dewar chamber, and the reflective surface and the emitting region face the aperture.

Other technical features may be readily apparent to one skilled in the art from the following figures, descriptions, and claims.

BRIEF DESCRIPTION OF THE DRAWINGS

For a more complete understanding of this disclosure, reference is now made to the following description, taken in conjunction with the accompanying drawings, in which.

DETAILED DESCRIPTION

FIGS. 1 through 9, described below, and the various embodiments used to describe the principles of the present disclosure in this patent document are by way of illustration only and should not be construed in any way to limit the scope of the disclosure. Those skilled in the art will understand that the principles of the present disclosure may be implemented in any type of suitably arranged device or system.

Systems utilizing infrared (IR) focal plane array (FPA) technology may undergo particle screen tests at the detector assembly level to check for large particles within the assembly. Some current particle screen tests capture video while subjecting an assembly to a series of shocks or vibrations. These tests are typically performed with a simple cover over an entrance window of the assembly. Cold particles within the assembly, if rattled loose by the shock or vibrations, can block the warm emission of the cover and cause an artifact to be seen in the video imagery. Because the cover is at a warm (ambient) temperature, the background irradiance on the detector is high, and sensitivity is therefore degraded compared to a tactical scene of an end-use sensor (typically a cold space scene for "space-based" systems such as kill vehicles, air-to-air missiles, satellites, etc.) due to a significantly shorter integration time used for the test.

To address these or other issues, embodiments of this disclosure provide a particle screen test at the detector assembly build level that improves sensitivity. The disclosed embodiments can use a shock and vibration environment that is the same as or similar to other particle screen tests. However, the disclosed embodiments include a narcissus mirror that is placed in the cover so that background irradiance is low enough to utilize the full integration time capability of the detector as described in greater detail below. Among the advantages of the disclosed embodiments is that the particle screen test is performed "in situ." That is, the detector assembly itself is used as the instrument that is looking for particles in the assembly. This is in contrast to other systems that rely on another camera or detector to perform the test.

Embodiments of this disclosure may be used in a variety of defense-related applications, such as with missile seekers, forward looking infrared (FLIR) systems, "kill" vehicles, or other missile defense systems. The disclosed embodiments may also be used in various commercial or non-defense applications, such as satellite systems or other space systems where shock or vibration at launch could disturb the system and redistribute particles in the system. In general, the disclosed embodiments can have application in any high-performance cooled IR system, including those that operate through rough environments where shocks and vibrations may dislodge particles. It will be understood that embodiments of this disclosure may include any one, more than one, or all of the features described here. In addition, embodiments of this disclosure may additionally or alternatively include other features not listed here.

Figure 1:
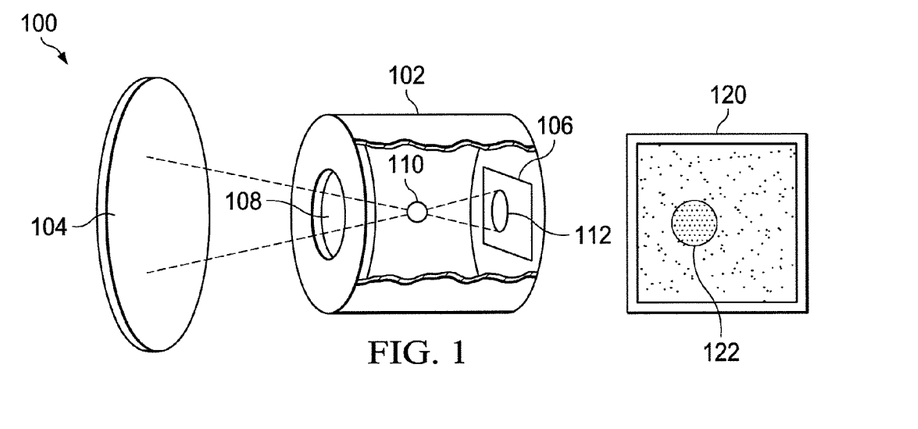
FIG. 1 illustrates an example detector assembly for a particle screen test that uses a warm scene according to this disclosure.

FIG. 1 illustrates an example detector assembly 100 for a particle screen test that uses a warm scene according to this disclosure. As shown in FIG. 1, the assembly 100 includes a dewar chamber 102, an assembly cover 104, and a detector focal plane array (FPA) 106. The dewar chamber 102 extends from the detector FPA 106 and forms a cavity in front of the detector FPA 106. The dewar chamber 102 (along with everything inside the cavity) is typically cryogenically cooled during a detection process. The dewar chamber 102 shields the detector from radiation originated from the surrounding ambient temperature surfaces. There may also be one or more spectral filters, lenses, prisms, baffles, glass, or other optical components (not shown) inside the cavity of the dewar chamber 102.

At the end of the dewar chamber 102 opposite the detector FPA 106 is an aperture 108 that limits the amount of radiation (such as visible and IR radiation) into the cavity of the dewar chamber 102. In some embodiments, the dewar chamber 102 is enclosed in a vacuum. This can require a sealed window that sits directly in front of the aperture 108. The window can be attached to an ambient temperature housing (therefore the window is also at ambient temperature) that surrounds the dewar chamber 102 and is sealed to hold a vacuum. This is used to prevent the cooled components from forming condensation, frost, or ice.

The dewar chamber 102 includes one or more particles to be detected, represented by a single particle 110 in FIG. 1. The particle 110 may be on a surface of the dewar chamber 102 or floating or moving inside the cavity of the dewar chamber 102. If there are optical components inside the cavity of the dewar chamber 102, the particle 110 may also be attached to one of these optical components. While only one particle 110 is shown here, there can be more than one detectable particle 110 inside the dewar chamber 102.

The assembly cover 104 is positioned in front of the aperture 108. During the detection process, the assembly cover 104 is typically at ambient temperature, which is much higher than the cryogenic temperatures inside the dewar chamber 102. Radiation from the assembly cover 104 passes through the dewar chamber 102 and is detected at the detector FPA 106. This results in the generation of one or more FPA images 120 that can be seen on a display. Compared to the cryogenically-cooled dewar chamber 102, warm IR radiation from the assembly cover 104 can generate a very bright saturated signal at the detector FPA 106. A portion of the IR radiation from the assembly cover 104 is blocked by the particle 110, which results in an area of reduced radiation 112 at the detector FPA 106. The area of reduced radiation 112 results in an artifact 122 in the FPA image 120. Due to the saturated signal caused by the warm IR radiation from the assembly cover 104, the artifact 122 caused by the particle 110 has low contrast and is not easily detected at the detector FPA 106.

Figure 2:
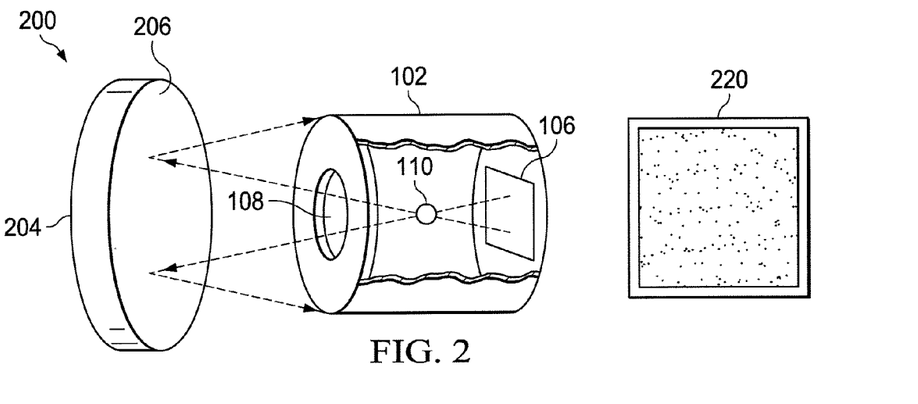
FIG. 2 illustrates an example detector assembly for a particle screen test that uses a low background scene produced using a narcissus mirror according to this disclosure.

FIG. 2 illustrates an example detector assembly 200 for a particle screen test that uses a low background scene produced using a narcissus mirror according to this disclosure. As shown in FIG. 2, the detector assembly 200 includes the dewar chamber 102, the detector FPA 106, and the aperture 108.

Unlike the detector assembly 100 of FIG. 1, the detector assembly 200 positions a narcissus mirror 204 in front of the aperture 108. In some embodiments, the narcissus mirror 204 can be positioned very close to the aperture 108, such as a few millimeters away from the aperture 108. A reflective surface 206 of the narcissus mirror 204 is low-emission and highly reflective and serves to reflect radiation from the cavity of the dewar chamber 102 back into the cavity. In particular embodiments, the reflective surface 206 is polished gold, although other suitable materials may be used.

Because the dewar chamber 102 and its contents are cryogenically cooled, the amount of radiation from the dewar chamber 102 that is reflected off the narcissus mirror 204 back into the dewar chamber 102 is small. This is in contrast to the larger amount of (ambient temperature) radiation from the assembly cover 104 in FIG. 1. The IR radiation from the cold dewar surfaces reflected off the narcissus mirror 204 passes through the dewar chamber 102 to the detector FPA 106. This results in one or more FPA images 220 that show dark low-saturation background signals. The background level of the FPA image 220 is still high but it takes a much longer integration time (exposure time) to get to this background level. This difference in integration time is what provides the increase in test sensitivity using the detector assembly 200.

Since the particle 110 is at substantially the same cryogenic temperature as the contents of the cavity of the dewar chamber 102, the reflected cavity radiation that is blocked by the particle 110 is at the same temperature as the particle 110 itself. Stated differently, the cold particle 110 blocks a portion of a cold scene reflected from the narcissus mirror 204. Thus, there is no difference in irradiance at the detector FPA 106. To the detector FPA 106, the cold particle 110 does not appear any different than the cold cavity of the dewar chamber 102. This can be seen in the FPA image 220, which shows no differences in irradiance due to the particle 110. Thus, the particle 110 is difficult or impossible to detect.

Figure 3:
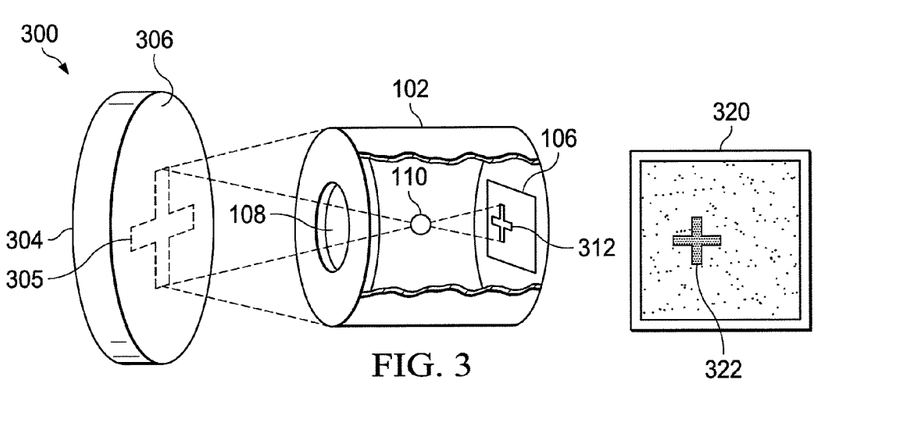
FIG. 3 illustrates an example detector assembly for a particle screen test that uses a cold scene produced using a narcissus mirror with an emitting region according to this disclosure.

FIG. 3 illustrates an example detector assembly 300 for a particle screen test that uses a cold scene produced using a narcissus mirror with an emitting region according to this disclosure. As shown in FIG. 3, the detector assembly 300 includes the dewar chamber 102, the detector FPA 106, and the aperture 108. The detector assembly 300 is configured for detection of one or more particles, which are represented by the single particle 110.

The detector assembly 300 here includes a narcissus mirror 304 positioned in front of the aperture 108. Like the narcissus mirror 204 of FIG. 2, the narcissus mirror 304 can be positioned very close to the aperture 108, such as a few millimeters away from the aperture 108. A reflective surface 306 of the narcissus mirror 304 is highly reflective and serves to reflect radiation from the cavity of the dewar chamber 102 back into the cavity. In particular embodiments, the reflective surface 306 is polished gold, although other suitable materials may be used.

In contrast to the narcissus mirror 204, the narcissus mirror 304 includes an emitting region 305 on the surface of the mirror 304. The emitting region 305 is a highly emissive region having much lower reflectivity than the surrounding reflective surface 306. In some embodiments, the emitting region 305 is a region of the mirror surface that is painted with a diffuse black low-reflectivity paint. In other embodiments, the emitting region 305 is a region of the mirror surface that is covered with low reflectivity paper, tape, or any other suitable material. In still other embodiments, the emitting region 305 includes one or more holes or openings that pass through the narcissus mirror 304. The emitting region 305 can include one or multiple different emissive formats, including paint, tape, an etched region, an anodized section, a hole or cavity, and the like.

As shown in FIG. 3, the emitting region 305 is in the shape of a reticle or cross pattern. The reticle pattern has relatively large dimensions across the pattern (such as from left to right and from top to bottom) but a relatively small total area. Of course, the reticle pattern is merely one example, and other shapes are possible for the emitting region 305. In general, a pattern for the emitting region 305 with relatively large dimensions but relatively small area could be preferred, but other designs of the emitting region 305 could be used.

Rather than reflecting portions of the cold image inside the dewar chamber 102, the emitting region 305 emits IR radiation at an ambient temperature. For example, when the emitting region 305 includes paint, tape, paper, or other surface covering, the emitting region 305 is generally at or near the same ambient temperature as the narcissus mirror 304. When the emitting region 305 includes holes through the narcissus mirror 304, the emitting region 305 allows IR radiation from a source behind the narcissus mirror 304 to pass through the narcissus mirror 304 (and generally such a source is also at ambient temperature). Thus, the emitting region 305 emits IR radiation associated with a warm scene.

The portions of the narcissus mirror 304 surrounding the emitting region 305 reflect cold IR radiation from the dewar chamber 102 back into the dewar chamber 102. However, the emitting region 305 emits warm IR radiation. If there was no particle present in the detector assembly 300, the warm IR radiation from the emitting region 305 and the reflected cold IR radiation from the surrounding regions would be part of a substantially constant background. The substantially constant background could be subtracted out over a time interval using non-uniformity correction or another suitable algorithm as known in the art. The resulting FPA image might look similar to the substantially uniform FPA image 220 of FIG. 2.

The presence of a particle 110 in the detector assembly 300 creates a different result. A portion of the warm IR radiation from the emitting region 305 is blocked by the particle 110. This results in a contrasting area of radiation 312 at the detector FPA 106. The contrasting area of radiation 312 results in an artifact 322 on one or more FPA images 320. The FPA image 320 shows the artifact 322, which is shaped like the emitting region 305 (a reticle shape in this example).

Essentially, the particle 110 blocks a portion of the signal that would otherwise come from the emitting region 305. This creates the contrasting area of radiation 312 at the detector FPA 106. Thus, the particle 110 acts similar to a pinspeck camera. In a pinspeck camera, an obstruction in the camera view causes a shadow of different points in the scene to fall on different points on the film. Similarly, in the detector assembly 300, the particle 110 blocks a portion of the signal, creating a difference or contrast from the background. The constant background is subtracted out using non-uniformity correction or another suitable algorithm as known in the art, and the result allows the artifact 322 to be detected more easily in the FPA image 320.

Unlike the low-contrast artifact 122 of FIG. 1, the contrast of the artifact 322 in FIG. 3 is very high because of a longer integration time used to put the background at the same count level. Detector systems operate using digital counts that can be integrated over time as known in the art. For example, an eight-bit detecting system allows 256 counts that can be stored before the detector is saturated. In a warm scene, this may correspond to integration over approximately one-tenth of a millisecond. However, in a cold scene, it may be able to integrate over several milliseconds. In FIG. 3, the primarily cold image reflected off the narcissus mirror 304 can be integrated for a longer time than the warm image radiated from the assembly cover 104 of FIG. 1. The longer integration time helps to increase the signal to noise (SNR) ratio in the detection system and creates a more distinct image for the artifact 322.

In some embodiments, the detector assembly 300 can be vibrated or shaken to mimic a shock or vibration environment, such as a missile or other object in flight. The vibrations or shaking movements can cause the particle 110 to move around inside the dewar chamber 102, thereby increasing the likelihood of detection.

Although FIGS. 1 through 3 illustrate various examples of detector assemblies for particle screen tests, various changes may be made to FIGS. 1 through 3. For example, the emitting region 305 in FIG. 3 could have other shapes, some of which are described below. Also, the makeup and arrangement of the detector assemblies are for illustration only. Components could be added, omitted, combined, or placed in any other configuration according to particular needs.

Figure 4:
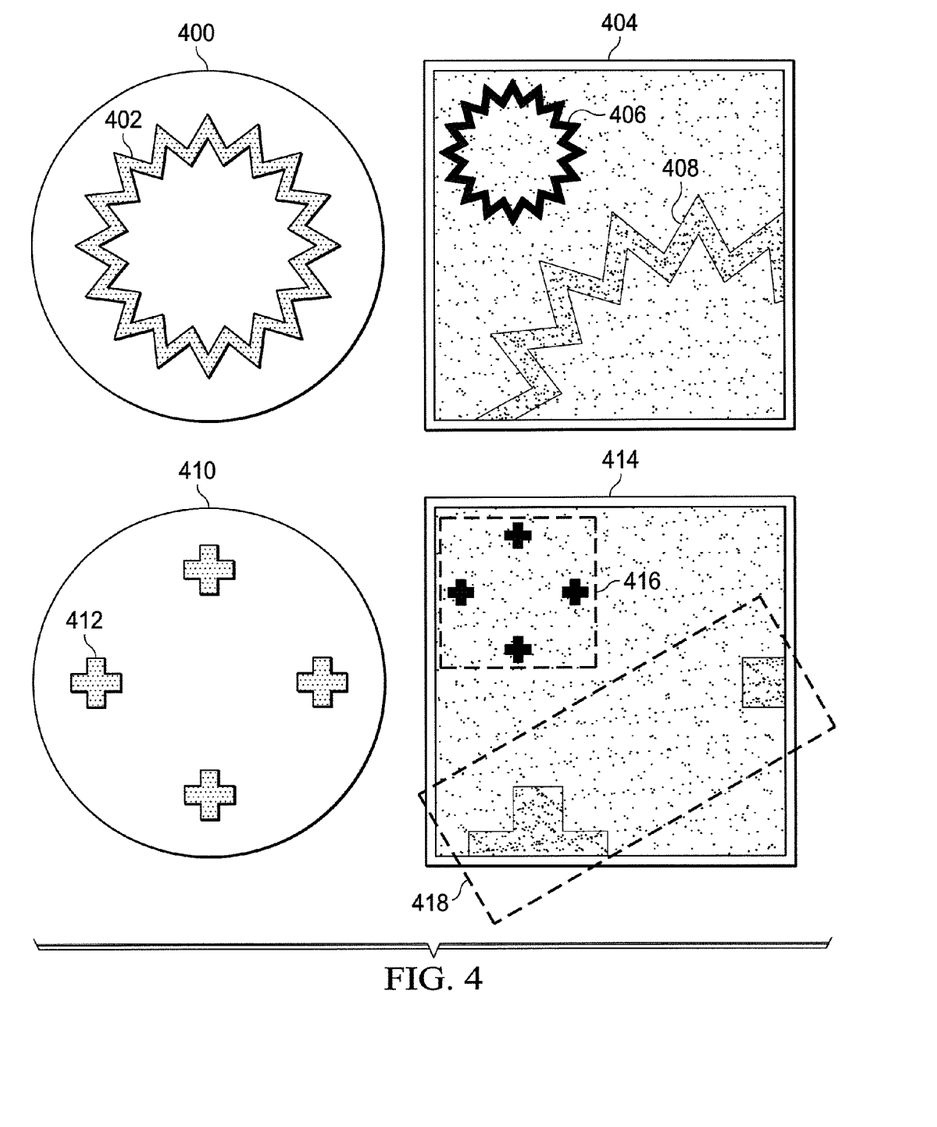
FIG. 4 illustrates additional examples of a narcissus mirror with an emitting region that can be used in a detector assembly according to this disclosure.

FIG. 4 illustrates additional examples of a narcissus mirror 400 and 410 with an emitting region 402 and 412 that can be used in a detector assembly according to this disclosure. The narcissus mirrors 400 and 410 of FIG. 4 can be used, for example, in the detector assembly 300 of FIG. 3.

The narcissus mirrors 400 and 410 illustrate that there are various options for the shape of the emitting region. For example, the narcissus mirror 400 has an emitting region 402 with a zig-zag line forming a circle. Note, however, that the shape of the emitting region does not need to be continuous, and there can be breaks or divisions in the emitting region. The emitting region can also include multiple separated parts. For example, the narcissus mirror 410 has an emitting region 412 that includes multiple separated sub-regions. In FIG. 4, the sub-regions are small reticle shapes.

The emitting regions 402 and 412 can be positioned and sized so that they can be seen by all pixels of the detector FPA 106 nearly uniformly. An emitting region could have a large overall outer dimension such that particles in the dewar chamber near edges of an imaging beam can be seen. That is, the outer diameter of the emitting region could generally line up with the outer edges of the aperture for a ray that intersects the particle such as is shown in FIG. 3. This provides the greatest spatial coverage within the dewar chamber 102 and the largest image at the detector FPA 106. The features of the emitting region could also be wide enough so that they are resolved by multiple pixels at the detector FPA 106 for the most likely particle location(s). The features of the emitting region should not be so small that they appear smaller than a single pixel at the detector.

While the overall dimensions of an emitting region could be large, the overall area of the shape or shapes forming the emitting region could be comparably small in order to keep the warm signal from the emitting region from saturating the detector FPA 106. Too much area would act similar to the structure in FIG. 1. Stated another way, the emitting region could subtend a small solid angle from the detector FPA in order to keep the background low.

Use of the emitting regions 402 and 412 could lead to the generation of FPA images 404 and 414, respectively. The FPA images 404 and 414 show two artifacts for two particles at different locations in the dewar chamber 102. In the FPA image 404, artifacts 406 and 408 result from different particles blocking the emitting region 402. In the FPA image 414, artifacts 416 and 418 result from different particles blocking the emitting region 412. The sizes of the artifacts at the detector FPA 106 is proportional to how far the particles are from the mirror. Bigger images indicate that particles are closer to the mirror. Thus, the artifact 406 results from a particle that is closer to the narcissus mirror 400 than another particle that generates the artifact 408. Similarly, the artifact 416 results from a particle that is closer to the narcissus mirror 410 than another particle that generates the artifact 418. The contrast is not as high in the larger artifacts 408 and 418 because the signal energy is spread over a larger area.

Although FIG. 4 illustrates additional examples of narcissus mirrors with emitting regions that can be used in a detector assembly, various changes may be made to FIG. 4. For example, narcissus mirrors with other emitting regions could be used in a detector assembly.

In addition to the embodiments shown in FIGS. 1 through 4, other embodiments according to this disclosure are possible. For example, instead of a narcissus mirror, a cold plate could provide the low emission background. The cold plate could be, for example, a liquid nitrogen-filled tank with a black absorbing wall. In such a case, the emitting region could be affixed to the cold plate or simply placed in front of the cold plate (e.g., between the cold plate and the aperture). Alternatively, the emitting region could be positioned to the side of the cold plate, and a fold mirror, prism, or beam splitter could be used to direct IR radiation emitted from the emitting region through the aperture.

In another example embodiment that uses a cold plate instead of a narcissus mirror, the detector assembly may not be cooled. That is, the dewar, particle, and FPA may all be at a warmer (e.g., ambient) temperature. In such a case, the warm particle blocks the cold view of the cold plate, thereby creating an artifact at the FPA image. Thus, an emitting region is not needed in this embodiment. However, in another embodiment, the detector assembly may be slightly cooler than ambient, such as with a thermoelectric (TE) cooler. In this embodiment, an emitting region can be used.

In yet another example embodiment, the detector assembly does not include a dewar and may not be an IR detector. Instead, the FPA detects a particle in a space between an IR radiation source or visible light source and the FPA. A dark (e.g., black) surface can be positioned in the background to increase the contrast.

Figure 5:
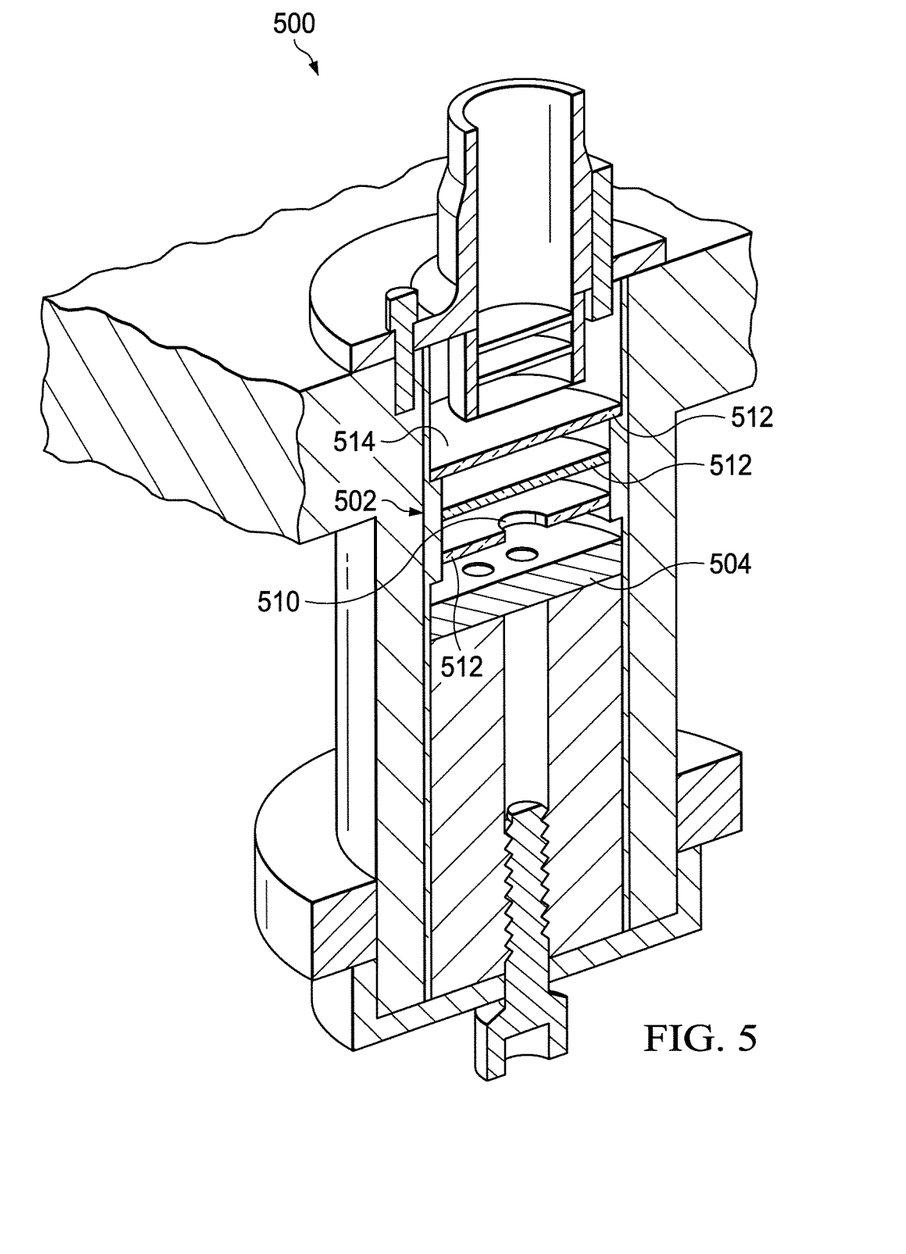
FIGS. 5 and 6 illustrate an example detector assembly that uses a narcissus mirror with an emitting region according to this disclosure.
Figure 6:
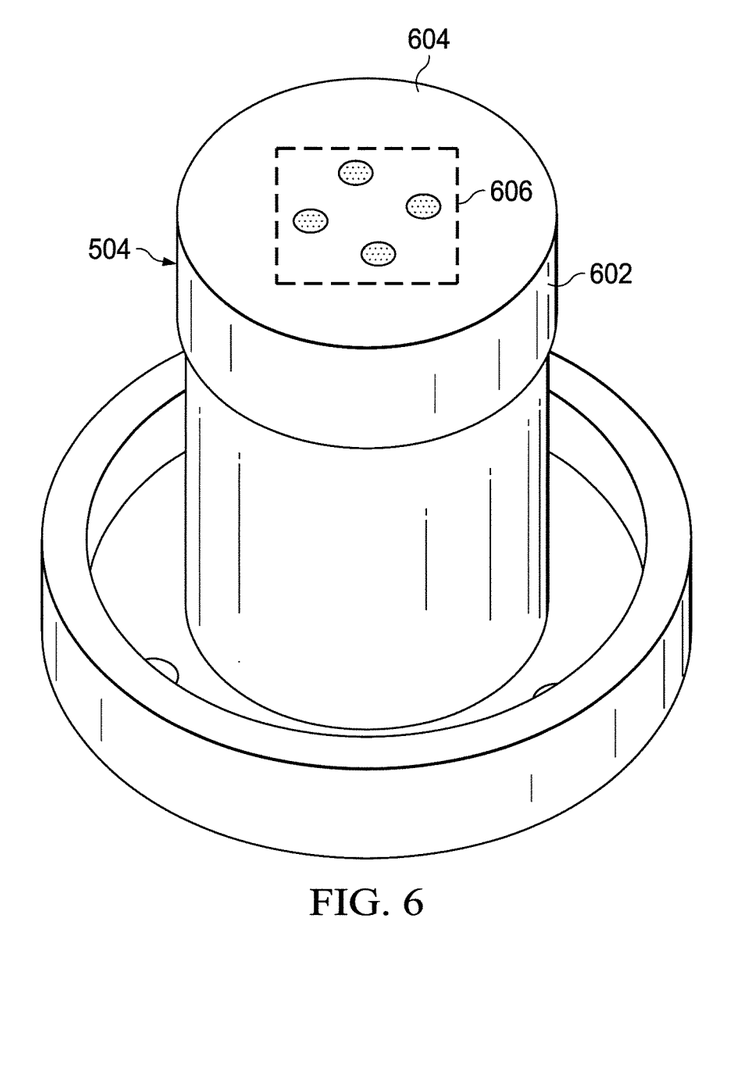

FIGS. 5 and 6 illustrate an example detector assembly 500 that uses a narcissus mirror with an emitting region according to this disclosure. The detector assembly 500 could represent (or be represented by) the detector assembly 300 of FIG. 3. FIG. 5 illustrates a cross-sectional view of the detector assembly 500. As shown in FIG. 5, the detector assembly 500 includes a dewar chamber 502 and a narcissus mirror 504. The dewar chamber 502 includes an aperture 510, optical elements 512, and a detector FPA 514. The narcissus mirror 504 is mounted close to the aperture 510. For example, in some embodiments, the reflective surface of the narcissus mirror 504 is positioned less than 0.1 inches away from the aperture 510. Of course, in other embodiments, the spacing may be more or less than 0.1 inches. In particular embodiments, the detector assembly 500 is mounted on a shaker table or another suitable base structure.

FIG. 6 illustrates a close-up view of the narcissus mirror 504. In some embodiments, the narcissus mirror 504 has an aluminum or other substrate 602 and a gold or other reflective surface 604. The narcissus mirror 504 also includes an emitting region 606 on its surface. In FIG. 6, the emitting region 606 includes four holes, such as holes that are approximately 0.3 inches apart. The size and position of the holes is generally a function of how large the aperture 510 is, how far the narcissus mirror 504 is from the aperture 510, how many pixels the detector has, and how sensitive the detector is. In other embodiments, the emitting region 606 could include tape, paint, an etched region, an anodized region, or other emissive format as described above.

Although FIGS. 5 and 6 illustrate one example of a detector assembly 500 that uses a narcissus mirror with an emitting region, various changes may be made to FIGS. 5 and 6. For example, the makeup and arrangement of the detector assembly 500 are for illustration only. Components could be added, omitted, combined, or placed in any other configuration according to particular needs.

Figure 7:
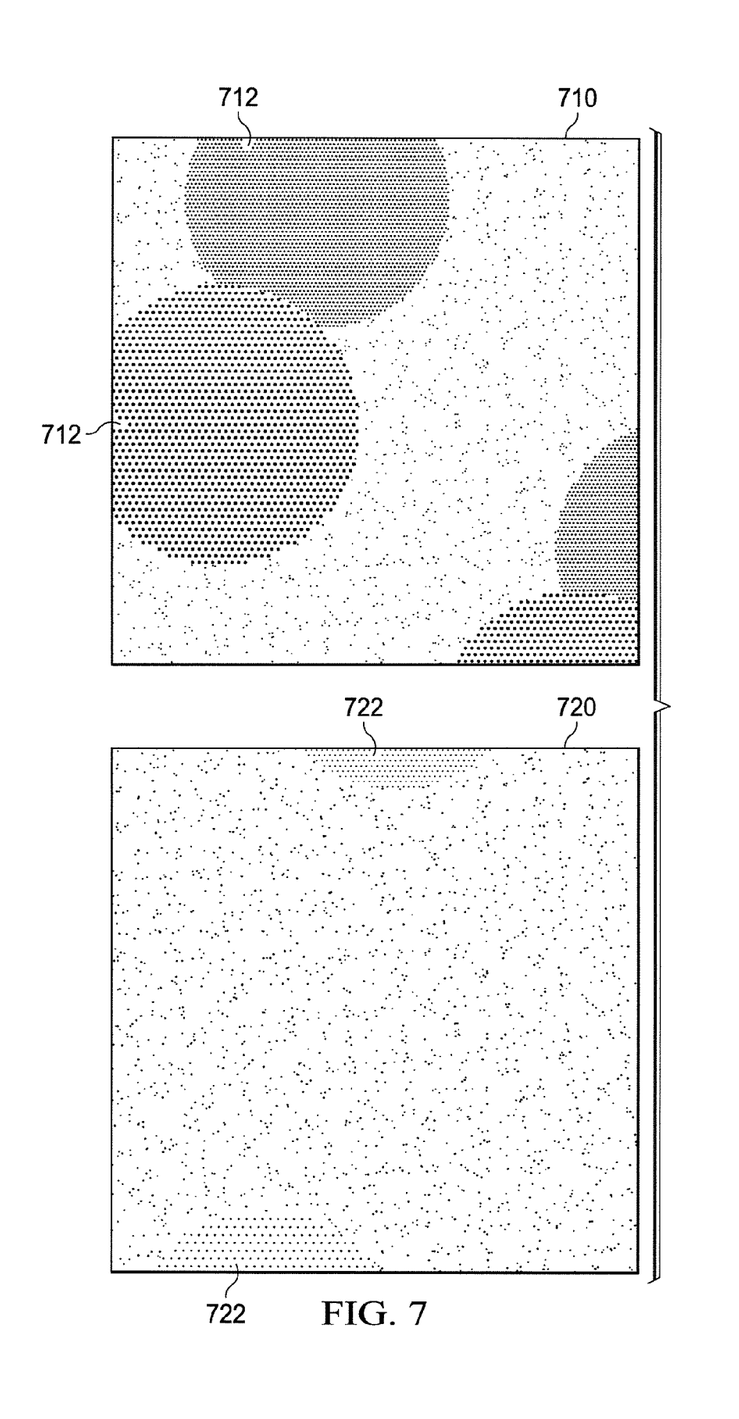
FIGS. 7 and 8 illustrate examples of test results of particle detection according to this disclosure.
Figure 8:
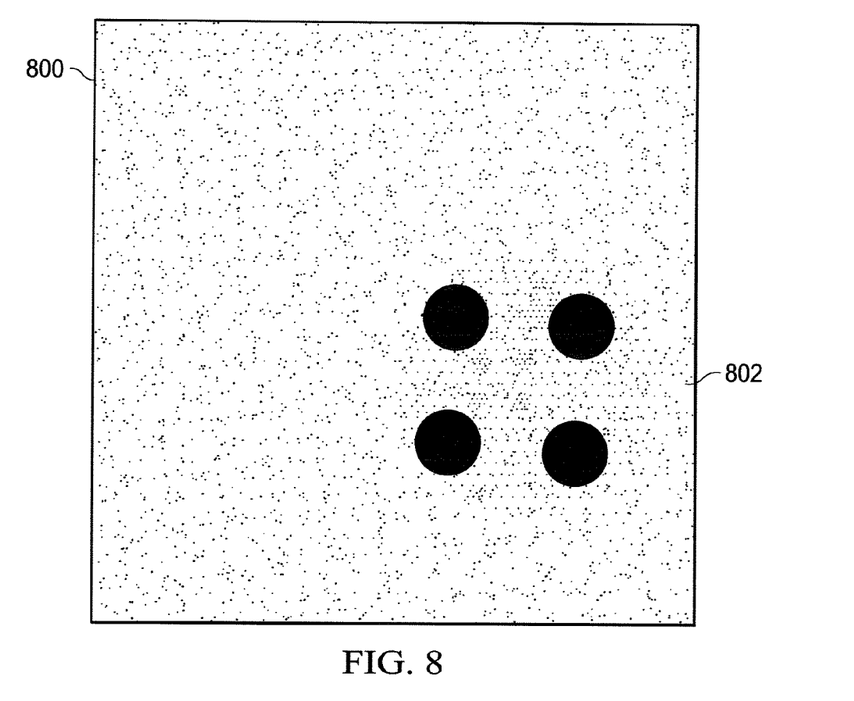

FIGS. 7 and 8 illustrate examples of test results of particle detection according to this disclosure. An FPA image 710 was generated in a test environment that includes larger particles, and the FPA image 710 includes artifacts 712 from the larger particles. An FPA image 720 was generated in a test environment that includes smaller particles, and the FPA image 720 includes artifacts 722 from the smaller particles.

In general, large particles are associated with a good signal to noise ratio (SNR), while small particles result in a poor SNR. When a particle is small, it becomes harder to detect. For example, the artifacts 722 are much less clear and distinct than the artifacts 712. If a particle is too small, it likely will not be detected at all by the particle detection test. However, a small particle can still be problematic in a run-time environment, such as when a scene is cold and the sensor is operating at maximum integration time.

In the test results shown in FIG. 8, the detector assembly includes a narcissus mirror with emitting region. For example, the test results shown in FIG. 8 may be captured using the detector assembly 500 of FIG. 5. In an FPA image 800, an artifact 802 is very distinct and visible.

Comparing FIG. 7 and FIG. 8, it can be seen that the detector assembly 500 is much more sensitive than the conventional particle detector assembly. The improvement in sensitivity is generally equal to the ratio of integration times of the "cold scene" divided by "warm scene." For example, a signal is proportional to the surface area of a particle so the reduction in detectable particle diameter (assuming a spherical particle shape) is the square root of the integration time ratio. Compared to a conventional particle detector, the detector assembly 500 can detect particles having a much smaller diameter. In some embodiments, the detector assembly 500 can detect particles approximate 2.5 times smaller than those detected using a conventional particle detector.

Although FIGS. 7 and 8 illustrate examples of test results of particle detection, various changes may be made to FIGS. 7 and 8. For example, the images in FIGS. 7 and 8 and the numerical values provided above are for illustration only.

Figure 9:
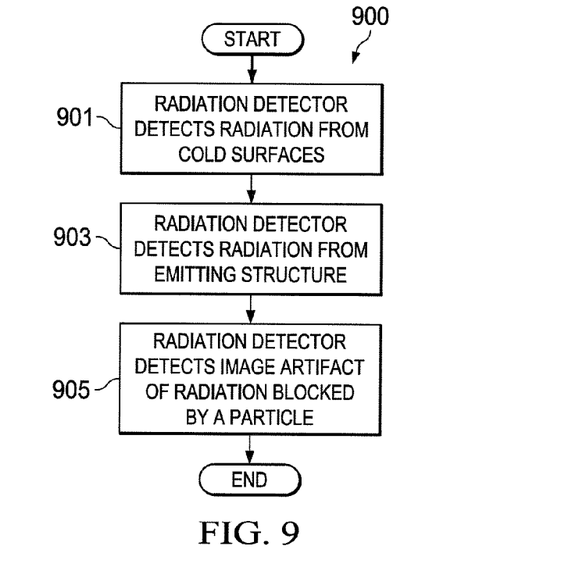
FIG. 9 illustrates an example method for high sensitivity particulate detection in a cooled infrared detector assembly according to this disclosure.

FIG. 9 illustrates an example method 900 for high sensitivity particulate detection in a cooled infrared detector assembly according to this disclosure. For ease of explanation, the method 900 is described as being used by the detector assembly 300 shown in FIG. 3, although the method 900 could be used with any other suitable system (such as the detector assembly 500).

At step 901, a radiation detector detects radiation originating in a dewar chamber and reflecting off a reflective surface of a mirror. This could include, for example, the detector FPA 106 detecting cryogenically cold surfaces emitting IR radiation originating in the dewar chamber 102 and reflecting off the reflective surface 306 of the narcissus mirror 304.

At step 903, the radiation detector detects radiation originating at or behind an emitting region of the mirror. This could include, for example, the detector FPA 106 detecting IR radiation originating at or passing through the emitting region 305.

At step 905, the radiation detector detects an image artifact resulting from a particle in the dewar chamber that blocks a portion of the "warm" radiation. This may include, for example, a particle 110 blocking a portion of the radiation from the emitting region 305, thereby causing an artifact (such as the contrasting area of radiation 312) at the detector FPA 106.

Although FIG. 9 illustrates one example of a method 900 for high sensitivity particulate detection in a cooled infrared detector assembly, various changes may be made to FIG. 9. For example, while shown as a series of steps, various steps shown in FIG. 9 could overlap, occur in parallel, occur in a different order, or occur multiple times. Moreover, some steps could be combined or removed and additional steps could be added according to particular needs.

It may be advantageous to set forth definitions of certain words and phrases used throughout this patent document. The terms "include" and "comprise," as well as derivatives thereof, mean inclusion without limitation. The term "or" is inclusive, meaning and/or. The phrase "associated with," as well as derivatives thereof, means to include, be included within, interconnect with, contain, be contained within, connect to or with, couple to or with, be communicable with, cooperate with, interleave, juxtapose, be proximate to, be bound to or with, have, have a property of, have a relationship to or with, or the like. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C.

The description in the present application should not be read as implying that any particular element, step, or function is an essential or critical element that must be included in the claim scope. The scope of patented subject matter is defined only by the allowed claims. Moreover, none of the claims is intended to invoke 35 U.S.C. §112(f) with respect to any of the appended claims or claim elements unless the exact words "means for" or "step for" are explicitly used in the particular claim, followed by a participle phrase identifying a function. Use of terms such as (but not limited to) "mechanism," "module," "device," "unit," "component," "element," "member," "apparatus," "machine," or "system" within a claim is understood and intended to refer to structures known to those skilled in the relevant art, as further modified or enhanced by the features of the claims themselves, and is not intended to invoke 35 U.S.C. §112(f).

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. A detector assembly comprising:
   a dewar chamber comprising an aperture and an infrared radiation detector; and
   a mirror disposed adjacent the aperture of the dewar chamber, the mirror having a reflective surface and an emitting region facing the aperture;
   wherein the infrared radiation detector is configured to detect first radiation and second radiation from the mirror, the first radiation originating from at least one relatively cold surface in the dewar chamber and reflecting off the reflective surface of the mirror, the second radiation originating from at least one relatively warm surface at or behind the emitting region, and
   wherein the infrared radiation detector is configured to detect an artifact caused by a particle in the dewar chamber that blocks a portion of the first or second radiation.

2. The detector assembly of claim 1, wherein the emitting region comprises at least one of:
   paint, paper, or tape applied to the reflective surface of the mirror;
   an etched region on the surface of the mirror; or
   an anodized region on the surface of the mirror.

3. The detector assembly of claim 1, wherein the emitting region comprises at least one hole passing through the mirror, and the at least one relatively warm surface from which the second radiation originates is disposed behind the at least one hole.

4. The detector assembly of claim 1, wherein the emitting region has a reticle shape.

5. The detector assembly of claim 1, wherein the emitting region comprises a plurality of separated sub-regions.

6. The detector assembly of claim 1, wherein:
   the aperture is at a first end of the dewar chamber; and
   the infrared radiation detector is disposed at a second end of the dewar chamber opposite the first end.

7. The detector assembly of claim 1, wherein:
   the dewar chamber is cryogenically cooled; and
   the mirror is at a higher temperature than the dewar chamber.

8. The detector assembly of claim 1, wherein the infrared radiation detector comprises an infrared focal plane array (FPA).

9. A method comprising:
   detecting, at an infrared radiation detector, first radiation originating from at least one relatively cold surface in a dewar chamber and reflecting off a reflective surface of a mirror;
   detecting, at the infrared radiation detector, second radiation originating from at least one relatively warm surface at or behind an emitting region of the mirror; and
   detecting, at the infrared radiation detector, an artifact caused by a particle in the dewar chamber that blocks a portion of the first or second radiation, wherein the infrared radiation detector is disposed in the dewar chamber, the dewar chamber comprising an aperture; and wherein the mirror is disposed adjacent the aperture of the dewar chamber, the reflective surface and the emitting region facing the aperture.

10. The method of claim 9, wherein the emitting region comprises at least one of:

paint, paper, or tape applied to the reflective surface of the mirror;

an etched region on the surface of the mirror; or an anodized region on the surface of the mirror.

11. The method of claim 9, wherein the emitting region comprises at least one hole passing through the mirror, and the at least one relatively warm surface from which the second radiation originates is disposed behind the at least one hole.

12. The method of claim 9, wherein the emitting region has a reticle shape.

13. The method of claim 9, wherein the emitting region comprises a plurality of separated sub-regions.

14. The method of claim 9, wherein:

the aperture is at a first end of the dewar chamber; and the radiation detector is disposed at a second end of the dewar chamber opposite the first end.

15. The method of claim 9, wherein:

the dewar chamber is cryogenically cooled; and the mirror is at a higher temperature than the dewar chamber.

16. The method of claim 9, wherein the infrared radiation detector comprises an infrared focal plane array (FPA).

17. A detector assembly comprising:

a cryogenically cooled dewar chamber comprising an aperture at a first end of the dewar chamber and an infrared radiation detector at a second end of the dewar chamber opposite the first end; and a mirror disposed adjacent the aperture of the dewar chamber, the mirror having a reflective surface and an emitting region facing the aperture, the mirror being at ambient temperature;

wherein the infrared radiation detector is configured to detect first radiation and second radiation from the mirror, the first radiation originating from at least one relatively cold surface in the dewar chamber and reflecting off the reflective surface of the mirror, the second radiation originating from at least one relatively warm surface at or behind the emitting region, and wherein the infrared radiation detector is configured to detect an artifact caused by a particle in the dewar chamber that blocks a portion of the first or second radiation.

18. The detector assembly of claim 17, wherein the emitting region comprises at least one of:

paint, paper, or tape applied to the reflective surface of the mirror;

an etched region on the surface of the mirror; or an anodized region on the surface of the mirror.

19. The detector assembly of claim 17, wherein the emitting region comprises at least one hole passing through the mirror, and the at least one relatively warm surface from which the second radiation originates is disposed behind the at least one hole.

20. The detector assembly of claim 17, wherein the emitting region has a reticle shape.

* * * * *